(12) United States Patent
Wheland et al.

(10) Patent No.: US 7,671,247 B2
(45) Date of Patent: Mar. 2, 2010

(54) METHODS FOR PURIFYING ALKANE LIQUIDS

(75) Inventors: Robert Clayton Wheland, Wilmington, DE (US); Leo Ernest Manzer, Wilmington, DE (US); Sheng Peng, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 468 days.

(21) Appl. No.: 11/520,319

(22) Filed: Sep. 13, 2006

(65) Prior Publication Data

US 2008/0064907 A1    Mar. 13, 2008

(51) Int. Cl.
C07C 7/163 (2006.01)

(52) U.S. Cl. .................... 585/258; 585/259; 585/260; 585/702; 585/820

(58) Field of Classification Search ......... 585/258–260, 585/350, 360, 820, 823–825, 841, 702
See application file for complete search history.

(56) References Cited

U.S. PATENT DOCUMENTS

| | | | |
|---|---|---|---|
| 2,819,289 A | 1/1958 | Oberhausen | |
| 3,216,924 A * | 11/1965 | McKinney et al. | 208/143 |
| 2005/0173682 A1 | 8/2005 | Zhang et al. | |

FOREIGN PATENT DOCUMENTS

| GB | 1 341 057 | 12/1973 |
|---|---|---|
| JP | 3-31304 | 2/1991 |
| RO | 101 217 | 6/1992 |
| RO | 101217 | 6/1992 |
| WO | WO 2005/114711 A1 | 12/2005 |
| WO | WO 2005/119371 A1 | 12/2005 |

OTHER PUBLICATIONS

Hiyoshi, N et al (2005). Applied Catalysis A: General, 288, 43-47.*
Lopez-Gejo, J. et al. (2007). J Micro/Nanolith., 6(3), 6 pgs.*
Lopez-Gejo, J. et al. (2007). Chem. Mater., 19, 3641-3647.*
Cameron, J.M.L. et al. (1945). J. Chem. Soc., 286-288.*
Hiyoshi, N. et al. (2006). Catalysis Letters, 106(3-4), 133-138.*
Hiyoshi, N. et al. (2006). Applied Catalysis A, 310, 194-198.*
Campbell, "Cyclohexane in Ullmann Encyclopaedia", 2005, Wiley.
PCT International Search Report and Written Opinion for International Application No. PCT/US2007/019829 dated Feb. 20, 2008.
Teteruk et al., Comparative Analysis of Hydrogenation and Adsorption Methods for Removal of Unsaturated Compounds From Hydrocarbon Feedstocks, SO Neftepererabotka I Neftekhimiya, Moscow, Russian Federation, 1988, vol. 7:18-19.
Switkes et al., Immersion Liquids for Lithography in the Deep Ultraviolet, Proceedings of SPIE, 2003, vol. 5040:690-699.

* cited by examiner

*Primary Examiner*—Robert J Hill, Jr.
*Assistant Examiner*—Brian McCaig
(74) *Attorney, Agent, or Firm*—Gail D. Tanzer

(57) ABSTRACT

Methods for purifying liquid alkanes are provided. The methods produce alkanes having low absorbance, particularly at 193 nm. The alkane liquids are useful as immersion liquids in photomicrolithography employed for production of electronic circuits.

14 Claims, No Drawings

METHODS FOR PURIFYING ALKANE LIQUIDS

FIELD OF THE INVENTION

The present invention is directed to the methods for preparing low absorbance alkane liquids useful as immersion liquids in photomicrolithography for production of electronic circuits.

BACKGROUND

Methods suitable for the purification of alkanes have long been known in the art. Such methods include hydrogenation to remove unsaturated impurities, adsorbent beds, zone refining, distillation and so forth.

Dumitrescu et al., Romanian Patent RO 101217, discloses the use of hydrogenation for removing unsaturated impurities from n-hexane.

Japanese Patent Application JP 03031304 A (abstract), discloses purification of hexanes by water washing, distillation, treatment in an adsorbent bed, followed by hydrogenation.

Teteruk et al. SO *Neftepererabotka i Neftekhimiya* (Moscow, Russian Federation) (1988), (7), 18-19 (abstract only), reports a comparison between hydrogenation and adsorption for the purification of hydrocarbons. The report concludes that adsorption is more effective.

Photolithographic methods have been employed for decades to fabricate electronic integrated circuits, and more recently, integrated optical circuit elements. One key enabling technology for fabricating ever-higher density integrated circuits has been the application of shorter and shorter wavelengths of exposure light, the smaller wavelengths permitting resolution of finer lines. Current technology employs ultraviolet (UV) wavelengths, generally below 250 nm, especially at 193 nm, in order to achieve the highest resolution possible in the present state of the art.

Recently it has been found that introduction of a high refractive index liquid in place of air between the photomask and the photosensitive target enables the production of higher resolution images while retaining 193 nm illumination. Switkes et. al., *Proceedings of SPIE*, Volume 5040, 699(2003) discusses so-called immersion photolithography. Water has been the immersion liquid of choice in photolithography with a 193 nm light source.

Low absorbance of the immersion liquid is of great importance. For a given degree of light transmission to the photosensitive target surface, lower absorbance equates to greater working distance, which is of great practical value. Furthermore, lower absorbance results in less radiative heating of the fluid. Because refractive index is temperature dependent, a change in temperature in the liquid can cause blurring of the image.

Hydrocarbons, especially alkanes, are known to exhibit refractive indices higher than that of water. For example, replacement of water as an immersion liquid by bicyclohexyl, with a refractive index of 1.64, would reduce the effective wavelength of 193 nm light to 118 nm. However, to be of practical use, immersion liquids must also be quite transparent. The absorbance requirements suitable for practical use appear to be ever tightening. For example, Zhang et al., U.S. Published Patent Application 2005/0173682, describe immersion fluids characterized by absorbance of 5 cm$^{-1}$ whereas today, practical absorbance is thought to lie at $\leq 0.10$ cm$^{-1}$.

Miyamatsu et al., WO2005/114711 (examples and claims only), disclose a process for preparing highly transparent alkanes by a combination of treatment with sulfuric acid and distillation.

French et al., WO2005/119371 discloses methods for purifying alkanes to achieve high transparency including hydrogenation and adsorbent treatment.

SUMMARY OF THE INVENTION

One embodiment of the present invention is a process comprising combining a composition comprising a liquid alkane and one or more unsaturated species with hydrogen, in the presence of a supported catalyst, under such conditions as to effect the hydrogenation of one or more of the unsaturated species to produce a reaction product comprising a hydrogenated alkane composition; filtering the reaction product; producing a filtrate; and contacting the filtrate with an adsorbent to produce an alkane composition having an absorbance at 193 nm of 0.1 cm$^{-1}$ or less.

DETAILED DESCRIPTION

As used herein, the term "alkane" encompasses at least one alkane, but may alternatively be used to refer to a plurality of alkanes in the same composition. A desirable result of the process of the invention is not contingent upon the separation of a plurality of otherwise highly purified alkanes into separate components.

Polycyclic alkanes are generally preferred for the combination of high refractive index and low vapor pressure. Particularly preferred are bicyclohexyl, exo-tetrahydrodicyclopentadiene, and decahydronaphthalene. More preferred are bicyclohexyl and exo-tetrahydrodicyclopentadiene. Most preferred is bicyclohexyl.

For the purposes of the present invention, the term "adsorbent" refers to a solid state material employed for the extraction of impurities from the liquid alkane composition employed in the present invention. Suitable adsorbents include silica, alumina (acidic, basic, or neutral), Zeolite molecular sieves (3A, 4A, 5A, or 13X), and carbon. Mixtures of adsorbents are also suitable. While the best choice of adsorbent may vary with substrate and particular impurities, in general, silica is preferred. Fine particle size such as 28-200 mesh chromatographic silica gel (Aldrich catalog #21,439-6) is preferred for high adsorption capacity while coarser particle size such as 8 mesh chromatographic silica gel (Aldrich catalog #24,982-3) is preferred for higher throughput.

Suitable adsorbents can be disposed in any convenient manner including fluidized beds, passive beds, columns, slurried into the composition comprising an alkane and the like. In one embodiment, the adsorbent is in a column through which the composition comprising an alkane is passed.

For the purposes of the present invention, the term "absorbance" refers to the thickness normalized decrease in transmitted light intensity through a specimen, as described by the equation, $$\alpha = [\ln(I_0/I)]/l$$

where $\alpha$ is absorbance, $I_0$ is the intensity of incident light, I, the intensity of transmitted light, and l is the optical path length through the specimen, in centimeters.

Alkane compositions prepared according to the process disclosed herein have an absorbance at 193 nm of $\leq 0.10$ cm$^{-1}$. For the purposes of the present invention, it is satisfactory to determine absorbance with a Varian Cary 5 UV/Vis/NIR spectrometer at 193 nm in glass cuvettes loaded under nitrogen.

In the present process, a hydrogenation step is followed by an adsorption step. The degree of hydrogenation required, and the extent of subsequent exposure to adsorbent, depend in part upon the nature of starting composition. Generally, the higher the contamination of the starting material, the longer the hydrogenation step, and the longer the exposure to adsorbent.

In some circumstances it may be desirable to perform distillation, filtration, zone-refining or other preparative purification prior to hydrogenation. In a preferred embodiment, the composition comprising an alkane used as the starting material in the process comprises at least 95%, more preferably at least 98% alkane and can be a mixture of alkanes.

Unsaturated species, olefins, ketones, aromatics and so forth, tend to be highly absorbing chromophores, and are common contaminants in alkanes. The purpose of hydrogenation is to reduce the concentrations of those species to low levels. Preferably, hydrogenation is conducted to a point at which unsaturated species are no longer detectable by gas chromatography/mass spectroscopy; that is, to a level below about 10 parts per million. Some, but not all, of the saturated analogs to the unsaturated contaminants originally present that remain after hydrogenation are much less absorbing, and therefore are of less concern as contaminants.

Hydrogenation is advantageously conducted in the presence of a catalyst. Suitable catalysts include, but are not limited to, ruthenium, palladium, platinum, Raney nickel, rhenium, and rhodium. Only inhomogeneous catalysis is suitable for the practice of the present invention since it is desirable to remove all catalyst after hydrogenation to keep light scattering as low as possible. In general it is expected that the best choice of catalyst will vary with the particular alkane to be purified and with the contaminants to be hydrogenated, and the choice can readily be made by one skilled in the art. It has been found in the practice of the invention that ruthenium on carbon is well-suited for use in the hydrogenation of bicyclohexyl compositions, and palladium on carbon is well-suited for use in the hydrogenation of exo-tetrahydrodicyclopentadiene compositions.

Hydrogenation can be conducted in the temperature range of 100-200° C. and at pressures in the range of 100-1000 psi (0.69-6.9 MPa) of hydrogen, preferably 500 to 1000 psi (3.5-6.9 MPa), for a period of 1 to 48 hours, preferably at least 5 hours. Hydrogenation is suitably carried out in a grease-free corrosion resistant autoclave that has been carefully cleaned prior to use. 200° C. is preferred for hydrogenation of bicyclohexyl compositions while 100° C. is preferred for exo-tetrahydrodicyclopentadiene compositions.

Filtration of the hydrogenated product may be accomplished using a sub-micron filter such as is commercially available from several sources. Alternatively, filtration can be accomplished by the adsorbent column itself, eliminating the necessity of a separate filtration step.

EXAMPLES

Absorbance was measured with a Varian Cary 5 UV/Vis/NIR spectrometer at 193 nm in glass cuvettes having optical path lengths specified in the specific examples. Cuvettes were loaded under nitrogen.

Catalysts employed were 5% Ruthenium on Carbon: (Aldrich catalog #20,618-0), 5% Platinum on Alumina: (Acros catalog #195260100), 5% Palladium on Carbon (Aldrich catalog #33,012-4), and 60 wt-% Nickel 60 on Kieselguhr (Aldrich catalog #20,878-7).

Liquid samples were stored and handled using TraceClean™ bottles supplied by VWR International, Inc., West Chester, Pa. 19380. Overall, liquid handling was done as much as possible under nitrogen using clean, grease free equipment.

Absorbance of as-received bicyclohexyl (Solutia 99.6%.) was >300 $cm^{-1}$ at 193 nm; that of exo-tetrahydrodicyclopentadiene (Dixie Chemical −99+%) was 16 $cm^{-1}$.

Example 1

2500 ml of bicyclohexyl as received was loaded into a 1 gallon Hastelloy® autoclave along with 5 grams of 5% ruthenium on carbon catalyst. The autoclave was chilled, evacuated, and pressured to 300 psi with hydrogen. The autoclave was heated to 200° C. while stirring, and then additional hydrogen was added as needed to establish and maintain a pressure of 1000 psi. After 5 hours the autoclave was cooled, the pressure released, and the bicyclohexyl recovered. The catalyst was filtered off in a nitrogen glove bag using nitrogen pressure to push the reaction mixture though a 0.45 micron polypropylene filter. The filtrate was filtered in three 800-900 g batches characterized respectively by absorbances of 0.24 $cm^{-1}$, 0.21 $cm^{-1}$, and 0.13 $cm^{-1}$ at 193 nm.

A 30 milliliter sample of 28-200 mesh chromatographic silica (Aldrich #21,439-6) was heated for 2 hours at 500° C. under a steady flow of air in a Hastelloy™ metal tube placed in a clamshell furnace. After two hours, nitrogen flow replaced the air flow; the tube was sealed, and was cooled to room temperature. The contents of the tube were emptied into a glass chromatography column in a nitrogen glove bag. The hydrogenated bicyclohexyl prepared above with absorbance of 0.13 $cm^{-1}$ was added to the top of the thus prepared chromatography column. The bicyclohexyl was allowed to wet down through the silica until liquid just started to exit the column. At that point all flow was stopped and the column was allowed to sit over night equilibrating in the nitrogen glove bag. The next morning flow was resumed and 24 30 ml fractions were collected. Fractions 1, 2, 3, 6, 9, 12, 15, 18, 24 were analyzed as shown in Table 1. ~1.2 psi $N_2$ was applied to the top of the column to increase flow rate. Absorbance was measured using a cuvette having a 10 cm optical path length.

TABLE 1

| Fraction | Absorbance ($cm^{-1}$) @ 193 nm | Optical Path Length |
| --- | --- | --- |
| 1 | 0.09 | 5 cm |
| 2 | 0.05 | 5 cm |
| 3 | 0.05 | 10 cm |
| 6 | 0.05 | 10 cm |
| 9 | 0.06 | 10 cm |
| 12 | 0.07 | 10 cm |
| 15 | 0.06 | 10 cm |
| 18 | 0.07 | 10 cm |
| 24 | 0.06 | 10 cm |

In total, over 720 ml of bicyclohexyl having absorbance <0.10 $cm^{-1}$ were collected from 30 ml of silica gel.

Example 2

800 ml of as-received bicyclohexyl was loaded into a 1.3 liter Hastelloy® autoclave along with 3.2 grams of 5 wt %

(dry basis) palladium on carbon catalyst wet with about half its weight in water. The autoclave was chilled, evacuated, and pressured to 300 psi with hydrogen. The autoclave was subject to rocking as it was heated to 200° C. Additional hydrogen was added as needed to establish and maintain a pressure of 1000 psi. After 5 hours the autoclave was cooled, the pressure released, and the bicyclohexyl recovered. The catalyst was filtered off in a nitrogen glove bag using nitrogen pressure to push the reaction mixture though a 0.45 micron polypropylene filter. The absorbance of the filtrate was 0.28 $cm^{-1}$ at 193 nm when measured using a cuvette having an optical path length of 1 cm.

The bicyclohexyl thus produced was run through a column containing 30 milliliter of 28-200 mesh chromatographic silica prepared as in Example 1. The procedures of Example 1 were repeated. Results are shown in Table 2.

TABLE 2

| Fraction | Asbsorbance ($cm^{-1}$) at 193 nm | Cuvette |
|---|---|---|
| 1 | 0.07 | 5 cm |
| 2 | 0.07 | 5 cm |
| 3 | 0.07 | 10 cm |
| 6 | 0.07 | 10 cm |
| 9 | 0.07 | 10 cm |
| 12 | 0.08 | 10 cm |
| 15 | 0.08 | 10 cm |
| 18 | 0.09 | 10 cm |

In total, over 540 ml of bicyclohexyl having absorbance <0.10 $cm^{-1}$ were collected from 30 ml of silica gel.

Comparative Example A

A silica gel column was prepared as in Example 1 except that 80 ml of 28-200 mesh chromatographic silica was employed. 800 ml of as-received bicyclohexyl was added to the top of the column, and the elution procedures of Example 1 were followed. The eluted bicyclohexyl was determined to have an absorbance of 85 $cm^{-1}$ at 193 nm using a cuvette having an optical path length of 0.25 mm.

The thus eluted bicyclohexyl was loaded into a 1.3 liter Hastelloy® autoclave along with 1.6 grams of 5% ruthenium on carbon catalyst (Aldrich) and the hydrogenation and filtration procedures followed in Example 2 were repeated. The filtrate so obtained was characterized by an absorbance of 0.13 $cm^{-1}$ at 193 nm determined using a cuvette having an optical path length of 5 cm.

Comparative Example B

A silica column was prepared as in Comparative Example A. Bicyclohexyl was added to the top of the column, and the elution procedures of Example 1 were followed. Collected fractions are shown in Table 3. 30 ml of bicyclohexyl characterized by absorbance <0.10 $cm^{-1}$ was obtained through 80 ml of silica.

TABLE 3

| Fraction | Volume | Absorbance ($cm^{-1}$) @ 193 nm | Optical Path length |
|---|---|---|---|
| 1 | ~30 ml | 0.08 | 1 cm |
| 2 | ~80 ml | 11.1 | 0.01 cm |
| 3 | ~80 ml | 62.8 | 0.01 cm |
| 4 | ~80 ml | 163 | 0.01 cm |
| 5 | ~80 ml | 230 | 0.01 cm |
| 6 | ~70 ml | 281 | 0.01 cm |

Comparative Example C

The hydrogenation and filtration procedures of Comparative Example A were repeated except that the catalyst was 1.6 grams of 5 wt-% platinum on alumina. The absorbance of the thus-hydrogenated filtrate was 0.71 $cm^{-1}$ at 193 nm when measured using a cuvette with a 1 cm optical path.

A silica column was prepared as in Example 1. The above hydrogenated bicyclohexyl was added to the top of the chromatography column, and the procedures of Example 1 were repeated. The fractions collected are shown in Table 4.

TABLE 4

| Fraction | Absorbance ($cm^{-1}$) @ 193 nm | Optical Path |
|---|---|---|
| 1 | 0.17 | 5 cm |
| 2 | 0.20 | 5 cm |
| 3 | 0.28 | 5 cm |
| 6 | 0.40 | 5 cm |
| 9 | 0.45 | 1 cm |
| 12 | 0.51 | 1 cm |
| 15 | 0.53 | 1 cm |
| 18 | 0.55 | 1 cm |

Comparative Example D

The hydrogenation and filtration procedures of Example 2 were repeated except that the catalyst was 2 grams of 60 wt % nickel on kieselguhr catalyst. The absorbance of the thus hydrogenated filtrate was 0.99 $cm^{-1}$ at 193 nm.

A silica column was prepared according to the procedures of Example 1. The above hydrogenated bicyclohexyl was added to the top of the chromatography column, and the procedures of Example 1 were repeated. The fractions collected are shown in Table 5.

TABLE 5

| Fraction | Absorbance ($cm^{-1}$) @ 193 nm | Optical Path Length |
|---|---|---|
| 1 | 0.17 | 5 cm |
| 2 | 0.33 | 5 cm |
| 3 | 0.40 | 2 cm |
| 6 | 0.55 | 2 cm |
| 9 | 0.62 | 2 cm |
| 12 | 0.68 | 2 cm |
| 15 | 0.72 | 2 cm |
| 18 | 0.71 | 2 cm |

Example 3

A silica column was prepared as in Comparative Example A except that 8 mesh silica (Aldrich #24,982-3) was employed instead of the 28-200 mesh Hydrogenated bicyclohexyl (5% Ru/C catalyst, 200° C., 1000 psi H2, 48 hrs, absorbance=0.15 $cm^{-1}$ at 193 nm) was added to the top of the chromatography column and the procedures of Example 1 were repeated except that the equilibration period was 2.5 days. The flow was resumed and the fractions shown in Table 6 were collected as 80 ml aliquots.

TABLE 6

| Fraction | Absorbance (cm$^{-1}$) @ 193 nm | Optical Path Length |
|---|---|---|
| 1 | 0.096 | 5 cm |
| 2 | 0.084 | 5 cm |
| 3 | 0.079 | 5 cm |
| 4 | 0.074 | 5 cm |

Example 4

A 1.3 liter Hastelloy® autoclave was loaded with 1.15 grams of 5% ruthenium on carbon catalyst and 600 ml of exo-tetrahydrodicyclopentadiene. The autoclave was chilled, evacuated, and pressured to 300 psi with H$_2$. The autoclave was heated to 100° C. while undergoing rocking, and additional hydrogen gas was added as needed to establish and maintain a pressure of 1000 psi. After 10 hours the autoclave was cooled, the pressure released, and the exo-tetrahydrodicyclopentadiene recovered. The catalyst was filtered off in a nitrogen glove bag using nitrogen pressure to push the reaction mixture though a 0.45 micron polypropylene filter. The absorbance of the filtrate was 0.49 cm$^{-1}$ at 193 nm when measured in a cuvette having a 1 cm optical path length.

A silica column was prepared using 80 ml of the 28-200 mesh chromatographic silica, following the method of Example 1. The above hydrogenated exo-tetrahydrodicyclopentadiene was added to the top of the chromatography column, and the elution procedures of Example 1 were followed. The next morning flow was resumed and the fractions described in Table 7 were collected:

TABLE 7

| Fraction | Volume | Absorbance (cm$^{-1}$) @ 193 nm | Optical Path Length |
|---|---|---|---|
| 1 | ~30 ml | 0.18 | 5 cm |
| 2 | ~80 ml | 0.10 | 5 cm |
| 3 | ~80 ml | 0.11 | 5 cm |
| 4 | ~80 ml | 0.12 | 5 cm |
| 5 | ~80 ml | 0.11 | 5 cm |
| 6 | ~80 ml | 0.13 | 5 cm |
| 7 | ~80 ml | 0.12 | 5 cm |
| 8 | ~80 ml | 0.12 | 5 cm |

Example 5

A 1.3 liter Hastelloy® autoclave was loaded with 2.3 grams of 5% palladium on carbon catalyst (Aldrich) and 600 ml of exo-tetrahydrodicyclopentadiene (Dixie Chemicals). The autoclave was chilled, evacuated, and pressured to 300 psi with H$_2$. The autoclave was heated to 100° C. while being rocked. Additional hydrogen gas was added as needed to establish and maintain a pressure of 1000 psi. After 5 hours the autoclave was cooled, the pressure released, and the exo-tetrahydrodicyclopentadiene recovered. The catalyst was filtered off in a nitrogen glove bag using nitrogen pressure to push the reaction mixture though a 0.45 micron polypropylene filter. The absorbance of the filtrate was 0.70 cm$^{-1}$ at 193 nm when measured in a cuvette having a 1 cm optical path length.

A silica column was prepared as in Comparative Example A. The hydrogenated exo-tetrahydrodicyclopentadiene prepared above was added to the top of the chromatography column, and eluted as in Comparative Example A. Fractions were collected as described in Table 8. Absorbance was determined using a cuvette with an optical path length of 5 cm.

TABLE 8

| Fraction | Volume | Absorbance (cm$^{-1}$) @ 193 nm |
|---|---|---|
| 1 | ~30 ml | 0.11 |
| 2 | ~80 ml | 0.10 |
| 3 | ~80 ml | 0.10 |
| 4 | ~80 ml | 0.10 |
| 5 | ~80 ml | 0.09 |
| 6 | ~80 ml | 0.10 |
| 7 | ~80 ml | 0.11 |
| 8 | ~80 ml | 0.10 |

Example 6

The hydrogenation and filtration procedures of Example 5 were repeated except that 1.15 grams of 5 wt-% Pt on alumina catalyst was employed in place of the Pd catalyst; and, the autoclave was held at 100° C. and 1000 psi H$_2$ pressure for 16 hours instead of 5 hours. The absorbance of the filtrate thus produced was 7.5 cm$^{-1}$ at 193 nm measured in cuvette having a 1 mm optical path length.

A silica column was prepared as in Comparative Example A, and the elution procedure thereof was followed using the above hydrogenated exo-tetrahydrodicyclopentadiene. The fractions shown in Table 9 were collected when flow was resumed. Absorbance was determined using a cuvette with a 5 cm optical path length.

TABLE 9

| Fraction | Volume | Absorbance (cm$^{-1}$) @ 193 nm |
|---|---|---|
| 1 | ~30 ml | 0.15 |
| 2 | ~80 ml | 0.10 |
| 3 | ~80 ml | 0.11 |
| 4 | ~80 ml | 0.13 |
| 5 | ~80 ml | 0.14 |
| 6 | ~80 ml | 0.15 |
| 7 | ~80 ml | 0.21 |
| 8 | ~80 ml | 0.28 |

Comparative Example E

The hydrogenation and filtration procedures of Example 5 were repeated except that 2 g of 60 wt % nickel on kieselguhr catalyst was employed in place of the Pd catalyst. The absorbance of the filtrate so produced was 0.52 cm$^{-1}$ at 193 nm measured with a cuvette having a 1 cm path length.

A silica column was prepared as in Comparative Example A, and the elution procedure thereof was followed using the above hydrogenated exo-tetrahydrodicyclopentadiene. The fractions shown in Table 10 were collected when flow was resumed. Absorbance was determined using a cuvette with a 5 cm optical path length.

TABLE 10

| Fraction | Volume | Absorbance (cm$^{-1}$) @ 193 nm |
|---|---|---|
| 1 | ~30 ml | 0.24 |
| 2 | ~80 ml | 0.13 |
| 3 | ~80 ml | 0.13 |

TABLE 10-continued

| Fraction | Volume | Absorbance (cm$^{-1}$) @ 193 nm |
|---|---|---|
| 4 | ~80 ml | 0.15 |
| 5 | ~80 ml | 0.24 |
| 6 | ~80 ml | 0.17 |
| 7 | ~80 ml | 0.16 |
| 8 | ~80 ml | 0.15 |

What we claim is:

1. A process comprising in a first step combining a composition comprising a liquid alkane and one or more unsaturated species with hydrogen, in the presence of a supported catalyst, at a temperature within the range of 100-200° C., at a pressures in the range of 100-1000 psi of hydrogen for a period of 1 to 48 hours, to produce a reaction product comprising a hydrogenated alkane composition; in a second step filtering the reaction product; producing a filtrate; and, in a third step contacting the filtrate with an adsorbent to produce an alkane composition having an absorbance at 193 nm of 0.1 cm$^{-1}$ or less.

2. The process of claim 1 wherein the liquid alkane comprises a polycyclic alkane.

3. The process of claim 2 wherein the polycyclic alkane is bicyclohexyl, exo-tetrahydrodicyclopentadiene, or decahydronaphthalene.

4. The process of claim 2 wherein the polycyclic alkane is bicyclohexyl, or exo-tetrahydrodicyclopentadiene.

5. The process of claim 4 wherein the polycyclic alkane is bicyclohexyl.

6. The process of claim 1 wherein the catalyst is selected from the group consisting of ruthenium, palladium, platinum, raney nickel, rhenium, and rhodium.

7. The process of claim 4 wherein the catalyst is ruthenium on carbon or palladium on carbon.

8. The process of claim 5 wherein the catalyst is ruthenium on carbon.

9. The process of claim 1 wherein the adsorbent is selected from the group consisting of silica, alumina (acidic, basic, or neutral), Zeolite molecular sieves (3A, 4A, 5A, or 13X), carbon, and mixtures thereof.

10. The process of claim 9 wherein the adsorbent is silica.

11. The process of claim 1 wherein the composition comprising a liquid alkane and unsaturated species comprises at least 98% by weight of a liquid alkane.

12. The process of claim 1 further comprising the step of distillation prior to hydrogenation.

13. The process of claim 1 wherein the liquid alkane comprises a plurality of alkanes.

14. The process of claim 1 wherein filtering and contacting with adsorbent are performed simultaneously.

* * * * *